US011051986B2

(12) United States Patent
Kendall

(10) Patent No.: US 11,051,986 B2
(45) Date of Patent: Jul. 6, 2021

(54) KNIT HEMOSTATIC BANDAGE

(71) Applicant: Beeken Biomedical LLC, Stoughton, MA (US)

(72) Inventor: Richard Kendall, Falmouth, MA (US)

(73) Assignee: Beeken Biomedical LLC, Stoughton, MA (US)

( * ) Notice: Subject to any disclaimer, the term of this patent is extended or adjusted under 35 U.S.C. 154(b) by 0 days.

(21) Appl. No.: 14/057,192

(22) Filed: Oct. 18, 2013

(65) Prior Publication Data

US 2014/0114224 A1 Apr. 24, 2014

Related U.S. Application Data

(60) Provisional application No. 61/716,264, filed on Oct. 19, 2012.

(51) Int. Cl.
*A61F 13/00* (2006.01)

(52) U.S. Cl.
CPC .. *A61F 13/00012* (2013.01); *A61F 13/00017* (2013.01); *A61F 2013/00238* (2013.01); *A61F 2013/00463* (2013.01)

(58) Field of Classification Search
CPC .......... A61F 13/00012; A61F 13/00017; A61F 13/0273; A61F 15/006; A61F 13/00–00046; A61F 13/02–0293; A61F 2013/00089–00357; A61F 13/06–148; A61F 2013/00361; A61F 2013/00365; A61F 2013/00463–00472; Y10S 2/903; Y10S 2/905; D04B 21/18; D04B 1/24; D04B 1/16; D04B 1/102; D04B 21/00; D04B 21/14–18; D04B 1/14–18; D04B 1/10

See application file for complete search history.

(56) References Cited

U.S. PATENT DOCUMENTS

| 2,511,685 | A | * | 6/1950 | Anderson | D04B 1/24 66/172 R |
| 3,040,551 | A | * | 6/1962 | Urlaub | D04B 35/34 66/197 |
| 4,034,751 | A | * | 7/1977 | Hung | A61F 13/00017 602/52 |
| 4,582,748 | A | * | 4/1986 | Eastes | E01D 19/041 248/562 |

(Continued)

FOREIGN PATENT DOCUMENTS

| CN | 2540171 | 3/2003 |
| CN | 101389318 | 3/2009 |
| RU | 66956 | 10/2007 |

OTHER PUBLICATIONS

Bryan Ellis et al., Polymers: A Property Database, 2008, CRC Press, 2nd Edition, p. 115-116 (Year: 2008).*

(Continued)

*Primary Examiner* — Keri J Nelson
*Assistant Examiner* — Michelle J Lee
(74) *Attorney, Agent, or Firm* — Fish & Richardson P.C.

(57) ABSTRACT

A knit hemostatic bandage provided herein can include a continuous rayon fiber and a continuous glass fiber. The knit hemostatic bandage can have a gauge of between 10 and 30 stitches per inch. The knit hemostatic bandage can have a Young's modulus of elasticity of less than 50 MPa.

16 Claims, 3 Drawing Sheets

(56) References Cited

U.S. PATENT DOCUMENTS

| | | | | |
|---|---|---|---|---|
| 4,665,909 | A * | 5/1987 | Trainor | A61F 13/0273 |
| | | | | 602/75 |
| 4,887,788 | A * | 12/1989 | Fischer | E01D 19/041 |
| | | | | 248/562 |
| 5,047,293 | A * | 9/1991 | Jansen | C08G 18/08 |
| | | | | 428/423.1 |
| 5,236,243 | A * | 8/1993 | Reyes | B60N 2/5833 |
| | | | | 24/442 |
| 6,194,629 | B1 * | 2/2001 | Bernhard | A61F 13/0273 |
| | | | | 128/882 |
| 2007/0021699 | A1 * | 1/2007 | Braunstein | A61F 5/0109 |
| | | | | 602/5 |
| 2007/0160653 | A1 * | 7/2007 | Fischer | A61F 13/00012 |
| | | | | 424/443 |
| 2008/0081763 | A1 * | 4/2008 | Swetlin | A61L 31/06 |
| | | | | 502/402 |
| 2012/0107388 | A1 * | 5/2012 | Oltarshevskaya | A61K 36/185 |
| | | | | 424/445 |

OTHER PUBLICATIONS

Chinese Office Action in Chinese Application No. 201380062036.6, dated Apr. 27, 2016, 12 pages (English Translation).
Chinese Office Action for Application No. 201380062036.6, dated Nov. 11, 2016, 14 pages (With English Translation).
Chinese Office Action in Application No. 201380062036.6, dated Jun. 20, 2017, 16 pages (With English Translation).
CA Office Action in Canadian Appln. No. 2,917,291, dated May 26, 2020, 3 pages.
CA Office Action in Canadian Appln. No. 2,917,291, dated Feb. 4, 2021, 3 pages.
International Search Report and Written Opinion in International Application No. PCT/US2013/065648, dated Jan. 30, 2014, 7 pages.

* cited by examiner

KNIT HEMOSTATIC BANDAGE

CROSS REFERENCE TO RELATED APPLICATIONS

This application claims the benefit of priority under 35 U.S.C. § 119(e) to U.S. Application No. 61/716,264 filed Oct. 19, 2012. The prior application is incorporated herein by reference in its entirety.

TECHNICAL FIELD

This document relates to knit hemostatic bandages.

BACKGROUND

A bandage is a piece of material used either to support a medical device such as a dressing or splint, or on its own to provide support to the body. During heavy bleeding it is important to slow the flow of blood. Despite considerable progress in understanding pathophysiological processes involved in surface (topical) hemostasis, continued blood loss through a bandage is still a major contributor to morbidity and mortality. Bandages are available in a wide range of types, from generic cloth strips, to specialized shaped bandages designed for a specific limb or part of the body. The standard of care is frequently the application of a tourniquet to control "compressible" bleeding and then gauze to control the residual "noncompressible" bleeding.

SUMMARY

A knit hemostatic bandage provided herein can include a continuous rayon fiber and a continuous glass fiber. The knit hemostatic bandage can have a gauge of between 10 and 15 stitches per inch. The knit hemostatic bandage can have a Young's modulus of elasticity of less than 0.8 GPa.

The details of one or more embodiments are set forth in the accompanying drawings and the description below. Other features, objects, and advantages will be apparent from the description and drawings, and from the claims.

DETAILED DESCRIPTION

Figure 1:
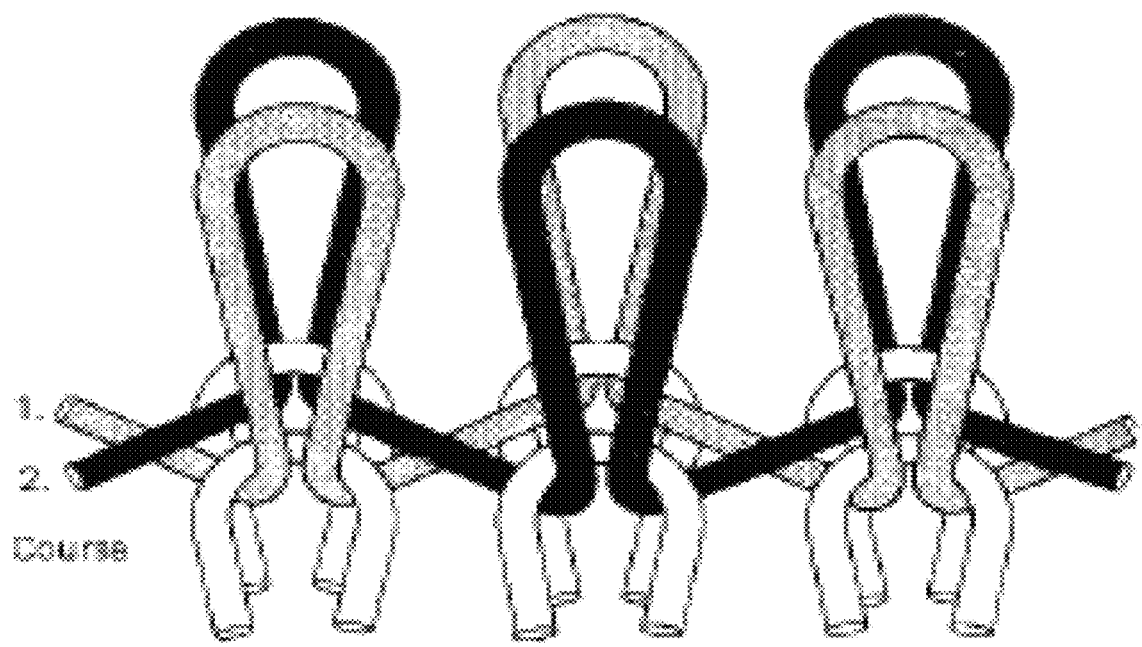
FIG. 1 illustrates how a glass fiber and a rayon fiber are knitted together in a knit hemostatic bandage as provided herein.

A knit hemostatic bandage can provide a healing response when applied to an open wound. The knit hemostatic bandage includes a knit structure of glass fiber and rayon fiber. The knit hemostatic bandage can display excellent hemostatic properties and fluid absorbency. In some cases, the knit hemostatic bandage can rapidly arrest bleeding, and is useful in situations where large hemorrhages exist or when a patient cannot be immediately admitted to a hospital or trauma treatment center.

In some cases, the knit hemostatic bandage can be stretchable. In some cases, the knit hemostatic bandage can have a Young's modulus of elasticity of less than 50 MPa (e.g., less than 40 MPa, less than 30 MPa, less than 20 MPa, less than 10 MPa, less than 5 MPa, less than 1 MPa, less than 0.5 MPa, less than 0.2 MPa, or less than 0.1 MPa). In some cases, the knit hemostatic bandage can have a Young's modulus of elasticity of between 10 MPa and 0.01 MPa, between 1 MPa and 05 MPa, or between 0.2 and 0.1 MPa. The knit structure of the knit hemostatic bandage can act like a coiled spring. The intertwining of loops of each stitch can give it functionality like a spring—when it is deformed it wants to return to its natural state. The stretch is not due to elasticity of the glass and rayon fibers themselves, but in how the loops of the glass and rayon fibers move in relation to each other. In some cases, the rayon fiber and the glass fiber can each have a Young's modulus of elasticity of 1 GPa or greater. For example, the rayon fiber can have a Young's modulus of elasticity of between 1 GPa and 30 GPa. For example, the glass fiber can have a Young's modulus of elasticity of between 70 GPa and 75 GPa. The glass and rayon fibers can remain intact when the knit hemostatic bandage is stretched. The stretch of the knit hemostatic textile can allow the bandage to be wrapped around an open wound with an amount of compression that improves the clotting of the wound.

The knit hemostatic bandage can include a continuous glass fiber. The glass fiber can be a fiberglass prepared by extrusion or electrospinning processes. In some cases, the glass fiber has fiber diameters from 5 nanometers to 15 microns. Types of glass contemplated for use in the knit hemostatic bandages provided herein include but are not limited to alumino-borosilicate glasses with low sodium oxide content, borosilicate glass, lead glass, aluminosilicate, alkali-barium silicate, vitreous silica, chalcogenide glass, phosphate glass, and bioactive glass sold under the trade name "BIOGLASS". The dimensions of the glass fiber component may be described by conventional nomenclature, including the following designations: B (3.5 micron diameter); C (4.5 micron diameter); D (5 micron diameter); DE (6 micron diameter); E (7 micron diameter); G (9 micron diameter); H (10 micron diameter); or K (13 micron diameter). In addition, strand count of the glass fiber component can range from 900 to 37. The grade of the glass fiber may be any of electrical grade ("E"), chemical grade ("C"), or high strength ("S"), and the filaments may be in any arrangement, for example continuous, staple, or textured. Fiberglass material is available commercially from various suppliers such as Owens Corning, and is available commercially as Grades G75, E-grade fiberglass, and the like, using the designations described above.

Rayon fibers used in the knit hemostatic bandages provided herein can impart absorbency, softness, and additional hemostatic activity to the bandage. As explained in more detail below, use of rayon fibers also aids in incorporating additional hemostatic factors to the bandage. In some cases, the rayon fibers can include bamboo rayon. In some cases, the rayon is derived from bamboo, cotton, rayon, linen, ramie, jute, sisal, flax, soybean, corn, hemp, lyocel, or a combination thereof. In some cases, one or more of the following fibers can be used instead or along with the rayon fibers: silk fibers; polyester fibers; nylon fibers; ceramic fibers; non-rayon polysaccharide fibers; animal fibers such as wool; lactide and/or glycolide polymers; lactide/glycolide copolymers; silicate fibers; polyamide fibers; feldspar fibers; zeolite fibers, zeolite-containing fibers; acetate fibers; and/or plant fibers that have been genetically engineered to express mammalian coagulation proteins or mammalian vasoactive factors. The rayon fibers may be prepared using conventional methods, including ring, open end (OE), rotor, or air jet spinning, and may have counts ranging from 1/1 to 100/1 Ne.

In some cases, a second rayon fiber is used to serge one or more edges of the bandage to keep it from unraveling. In some cases, the knit hemostatic bandages provided herein can have rayon fibers in the main body having a first yarn size and rayon fibers used to serge the edge of a second yarn size. For example, a knit hemostatic bandage can have bamboo rayon in the main body of the bandage having a 30/1 yarn size and bamboo rayon used to serge the edge having a 8/1 yarn size. Yarn size is a measurement of the length of yarn you get from one pound of fiber when it is spun.

The knit hemostatic bandage can be knit using a variety of arrangements. In some cases, each bandage can include a continuous length of one glass fiber and one rayon fiber. In some cases, each row of the knit can include at least a portion of a glass fiber and at least a portion of a rayon fiber. Referring to FIG. 1, each row of the knit can include a glass fiber 1 and a rayon fiber 2. As shown in FIG. 1, the glass fiber and the rayon fiber can alternate between a front and rear position with each subsequent stitch. In some cases, the glass fiber is stitched to the rayon fibers of the adjacent rows. In some cases, the glass fiber is stitched to glass fiber of the adjacent rows and the rayon fiber is stitched to rayon fiber of the adjacent rows. In some cases, the rows of each bandage are formed by folding the glass fiber and the rayon fiber back and forth for each row.

The knit hemostatic bandage can have between 10 and 30 stitches per inch, which is sometimes referred to as the gauge of the knit. In knitting, the word gauge is used to refer to the number of stitches per inch. In machine knitting, gauge can be determined by counting the number of needles on a knitting machine bed over several inches then dividing by the number of inches in the width of the sample. In some cases, the gauge of the knit hemostatic bandage is about 20 stitches per inch. In some cases, the knit hemostatic bandage can have between 10 and 15 stitches per inch. In some cases, the gauge of the knit hemostatic bandage is about 12 stitches per inch. The gauge of the knit hemostatic bandage can depend on the pattern of stitches in the fabric, the thickness of the fibers, and the tension.

The relative amounts of glass fibers and rayon fibers can range widely. In some cases, a knit hemostatic bandage can include approximately equal lengths (i.e., within 10%) of glass fiber and rayon fiber. In some cases, the knit hemostatic bandages provided herein include from about 30 to 80 wt % glass fibers and about 70 to 20 wt % rayon fibers, from about 50 to 80 wt % glass fibers and about 50 to 20 wt % rayon fibers, from about 60 to 70 wt % glass fibers and about 40 to 30 wt % rayon fibers, or about 65 wt % glass fibers and about 35 wt % rayon fibers.

The knit hemostatic bandage can be knit by a knitting machine. In some cases, a lubricant can be applied to the glass fiber and/or the rayon fiber prior to the knitting operation. The lubricant can then be removed after the knitting to ensure that surfaces of the fibers are exposed to induce hemostatic systems of a body of an animal (e.g., a human). The lubricant can be a mixture of starch, oil, and other ingredients, which can help to keep the filament glass from fraying and breaking during a weaving processes. In some cases, the lubricant is less than 5 weight percent of the stock glass filament. The wash process can include immersing the bandage in an aqueous solution. The aqueous solution can include Non Ionic Detergents, soda ash, and enzymes. The bandage can be washed in the solution for 20 minutes at a temperature of about 150° F. The solution can then be drained and the washing process repeated for another wash lasting 10 minutes. The washing process can break down any starch and oil-based lubricant on the surface of the fibers, ensuring a clean surface free of contaminants. The cleanliness of the fibers contributes to the functionality of the bandage by allowing the surface of the glass and rayon material to come directly in contact with blood and other biologic tissue.

As discussed in US 2007/0160653 A1, which is hereby incorporated herein, a combination of glass fiber and rayon fibers can activate hemostatic systems. The knit hemostatic bandages provided herein can stretch and thus compression when wrapped around a wound. The knit structure can be used to provide an appropriate amount of compression to the wound to improve the hemostatic properties of the combination of glass fiber and rayon fiber.

The knit hemostatic bandage can be applied directly to an open wound such that blood from an injured subject (e.g., a human with an open wound) contacts the glass and/or rayon fibers of the bandage. As discussed in US 2007/0160653 A1, platelets in the injured subject's blood can bind to the fibers.

In some cases, the hemostatic properties of the knit hemostatic bandage can include additional blood factors such as thrombin, lyophilized blood cells, lyophilized platelets, fibrin, fibrinogen, or combinations of these, to increase the hemostatic properties of the knit hemostatic bandage. These additional factors aid in activating the body's natural hemostasis cascade and result in a material that can rapidly arrest bleeding.

The knit hemostatic bandage can have a variety of dimensions. In some cases, the knit hemostatic bandage can have a width of between 1 inch and 6 inches and a length of at least 8 inches. In some cases, the knit hemostatic bandage can have a width of about 4 inches and a length of about 48 inches. In some case, the bandage can be wrapped in a roll and packaged. The packaged bandage can be sterilized. The bandage can be substantially free of lubricants, adhesives, or surface coatings. In some cases, the bandage can include multiple plies of the knit structure describe herein.

EXAMPLES

An example of a knit hemostatic bandage includes a continuous E-alumino-borosilicate glass fiber having a diameter of about 6.5 microns knitted with a continuous bamboo rayon fiber having a diameter of about 11 microns. The knit structure has the arrangement shown in FIG. 1 with about 12 stitches per inch. The knit structure can have a Young's modulus of approximately 0.13 MPa (0.00013 GPa). The knit hemostatic bandage has a thickness of about 1-2 mm, a width of about 4 inches, and a length of between 8 and 100 inches. The knit hemostatic bandage is rolled up and packaged in a sterilized package. The sterilized package can be a paper and plastic film pouch. The knit hemostatic bandage can be sterilized by either ethylene oxide (EtOH) gas or gamma irradiation.

Figure 2:
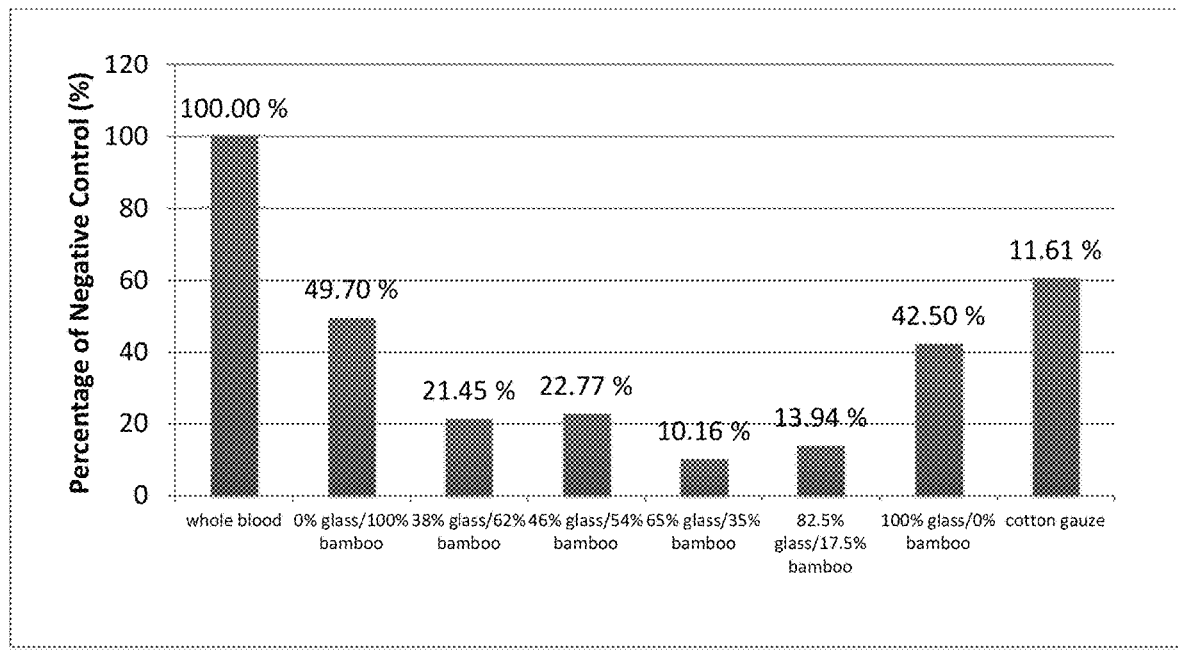
FIGS. 2 and 3 are charts showing clotting times normalized as a percentage of a negative control (whole blood).

FIG. 2 depicts clotting times normalized as a percentage of the negative control (whole blood) for different blends of glass and bamboo fiber (bamboo rayon), for 100% bamboo fiber, for 100% glass, and for cotton gauze using a first batch of blood. As shown, a combination of glass fiber and bamboo fiber provided improved clotting times.

Figure 3:
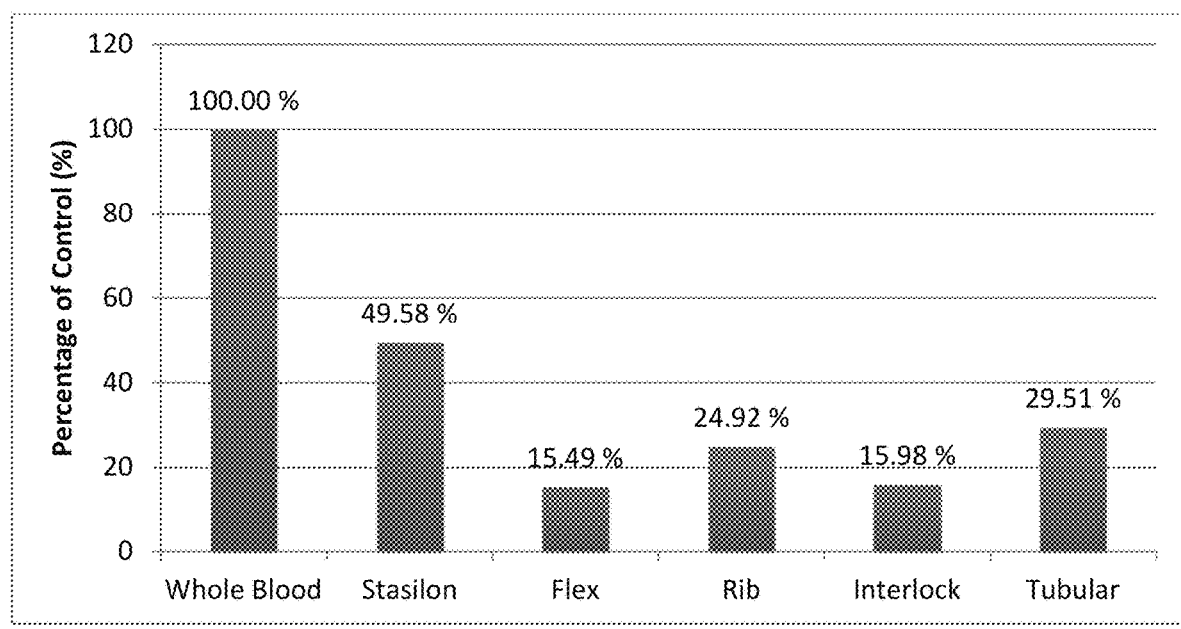

FIG. 3 depicts clotting times normalized as a percentage of the negative control (whole blood) for different blends made using different construction methods using a second batch of blood. Stasilon has a woven configuration. Flex, Rib, Interlock, and Tubular are all knitted configurations. Stasilon, Flex, Interlock, Tubular and Rib are all a 65/35 blend. Table 1 below shows the knit structure of the Interlock, Rib, and Tubular constructions. Flex uses the same type of knot structure as Interlock. As shown, the differences and how the material is woven or knitted has some effect on the performance of the bandage and the knit structures of Flex, Rib, Interlock, and Tubular provide improved clotting times as compared to the woven structure of Stasilon.

|  | Min | Max | Avg |
|---|---|---|---|
| Combined |  |  |  |
| Wales (thread per inch across the width) | 15 | 21 | 18 |
| Courses (threads per inch across the length) | 19 | 28 | 25 |
| Ball Burst Strength (lbsf)) | 80 | 245 | 157 |
| % elongation | 91 | 185 | 136 |
| Interlock |  |  |  |
| Wales (thread per inch across the width) | 18 | 21 | 20 |
| Courses (threads per inch across the length) | 19 | 25 | 22 |
| Ball Burst Strength (lbsf) | 149 | 166 | 154 |
| % elongation | 140 | 168 | 154 |
| Rib |  |  |  |
| Wales (thread per inch across the width) | 16 | 20 | 17 |
| Courses (threads per inch across the length) | 21 | 28 | 26 |
| Ball Burst Strength (lbsf) | 80 | 157 | 114 |
| % elongation | 148 | 185 | 163 |
| Tubular |  |  |  |
| Wales (thread per inch across the width) | 18 | 21 | 20 |
| Courses (threads per inch across the length) | 25 | 27 | 26 |
| Ball Burst Strength (lbsf) | 180 | 245 | 214 |
| % elongation | 91 | 99 | 95 |
| Sock |  |  |  |
| Wales (thread per inch across the width) | — | — | 13 |
| Courses (threads per inch across the length) | — | — | 12 |
| Ball Burst Strength (lbsf) | — | — | — |
| % elongation | — | — | — |

A number of embodiments have been described. Nevertheless, it will be understood that various modifications may be made without departing from the spirit and scope of the invention. For example, a knit hemostatic bandage can include a non-rayon plant fiber, such as raw cotton, in some cases. Accordingly, other embodiments are within the scope of the following claims.

What is claimed is:

1. A knit hemostatic bandage comprising:
    a continuous rayon fiber and a continuous glass fiber formed into rows, each row having multiple stitches, wherein the continuous rayon fiber has a Young's modulus of elasticity of between 1 GPa and 30 GPa and the continuous glass fiber has a Young's modulus of elasticity of between 70 GPa and 75 GPa,
    each stitch of the knit hemostatic bandage comprising a loop of the continuous rayon fiber and a loop of the continuous glass fiber, wherein the loop of the continuous rayon fiber has a Young's modulus of elasticity of between 1 GPa and 30 GPa and the loop of the continuous glass fiber has a Young's modulus of elasticity of between 70 GPa and 75 GPa, in which, for each stitch in a row:
    the loop of the continuous rayon fiber is stitched to only one of the loops of an adjacent stitch in an adjacent row and the loop of the continuous glass fiber is stitched to only the other one of the loops of the adjacent stitch in the adjacent row,
    the stitches in each row alternating between (i) a first configuration in which the loop of the continuous rayon fiber is disposed toward a first face of the knit hemostatic bandage and the loop of the continuous glass fiber is disposed toward a second face of the knit hemostatic bandage, the second face opposite the first face, and (ii) a second configuration in which the loop of the continuous rayon fiber is disposed toward the second face of the knit hemostatic bandage and the loop of the continuous glass fiber is disposed toward the first face of the knit hemostatic bandage, the knit hemostatic bandage having a gauge of between 10 and 30 stitches per inch, and
    wherein due to a relative motion of the loops of the continuous rayon fiber and the loops of continuous glass fiber that occurs responsive to deformation of the knit hemostatic bandage, the knit hemostatic bandage is provided with an overall Young's modulus of elasticity of between 0.05 MPa and 1 MPa.

2. The knit hemostatic bandage of claim 1, wherein the bandage has a gauge of between 10 and 15 stitches per inch.

3. The knit hemostatic bandage of claim 2, wherein the bandage has a gauge of 12 stitches per inch.

4. The knit hemostatic bandage of claim 1, wherein the continuous rayon fiber comprises a first rayon fiber, and comprising a second rayon fiber, the second rayon fiber stitched at an edge of the knit hemostatic bandage to serge the edge of the knit hemostatic bandage.

5. The knit hemostatic bandage of claim 4, wherein the first rayon fiber has a smaller yarn size than the second rayon fiber.

6. The knit hemostatic bandage of claim 1, wherein the bandage has a gauge of 20 stitches per inch.

7. The knit hemostatic bandage of claim 1, wherein the bandage has a width of between 1 and 6 inches.

8. The knit hemostatic bandage of claim 1, wherein the knit structure includes glass fiber and rayon fiber in each row.

9. The knit hemostatic bandage of claim 1, wherein the rayon fiber is cellulose rayon.

10. The knit hemostatic bandage of claim 1, wherein the rayon fiber is bamboo rayon.

11. The knit hemostatic bandage of claim 1, wherein the continuous rayon fiber is formed of a rayon that exhibits hemostatic activity.

12. The knit hemostatic bandage of claim 1, comprising one or more of thrombin, lyophilized blood cells, lyophilized platelets, fibrin, and fibrinogen.

13. The knit hemostatic bandage of claim 1, wherein the continuous rayon fiber and the continuous glass fiber formed into rows form a ply of the bandage, and wherein the knit hemostatic bandage comprises multiple plies.

14. A knit hemostatic bandage comprising:
    a continuous secondary fiber and a continuous glass fiber formed into rows, each row having multiple stitches, wherein the continuous secondary fiber has a Young's modulus of elasticity of between 1 GPa and 30 GPa and the continuous glass fiber has a Young's modulus of elasticity of between 70 GPa and 75 GPa,
    each stitch of the knit hemostatic bandage comprising a loop of the continuous secondary fiber and a loop of the continuous glass fiber, wherein the loop of the continuous secondary fiber has a Young's modulus of elasticity of between 1 GPa and 30 GPa and the loop of the continuous glass fiber has a Young's modulus of elasticity of between 70 GPa and 75 GPa, in which, for each stitch in a row:
    the loop of the continuous secondary fiber is stitched to only one of the loops of an adjacent stitch in an adjacent row and the loop of the continuous glass fiber is stitched to only the other one of the loops of the adjacent stitch in the adjacent row, the stitches in each row alternating between (i) a first configuration in which the loop of the continuous secondary fiber is disposed toward a first face of the knit hemostatic bandage and the loop of the continuous glass fiber is disposed toward a second face of the knit hemostatic bandage, the second face opposite the first face, and (ii) a second configuration in which the loop of the continuous secondary fiber is disposed toward the second face of the knit hemostatic bandage and the loop of the continuous glass fiber is disposed toward the first face of the knit hemostatic bandage, wherein due to a relative motion of the loops of the continuous secondary fiber and the loops of continuous glass fiber that occurs responsive to deformation of the knit hemostatic bandage, the knit hemostatic bandage is provided with an overall Young's modulus of elasticity of between 0.05 MPa and 1 MPa.

15. The knit hemostatic bandage of claim 14, wherein the continuous secondary fiber is a continuous rayon fiber.

16. A knit hemostatic bandage comprising:

a continuous secondary fiber and a continuous glass fiber formed into rows, each row having multiple stitches, wherein the continuous secondary fiber has a Young's modulus of elasticity of between 1 GPa and 30 GPa and the continuous glass fiber has a Young's modulus of elasticity of between 70 GPa and 75 GPa, each stitch of the knit hemostatic bandage comprising a loop of the continuous secondary fiber and a loop of the continuous glass fiber, wherein the loop of the continuous secondary fiber has a Young's modulus of elasticity of between 1 GPa and 30 GPa and the loop of the continuous glass fiber has a Young's modulus of elasticity of between 70 GPa and 75 GPa, in which, for each stitch in a row:

the loop of the continuous secondary fiber is stitched to only one of the loops of an adjacent stitch in an adjacent row and the loop of the continuous glass fiber is stitched to only the other one of the loops of the adjacent stitch in the adjacent row, the stitches in each row alternating between (i) a first configuration in which the loop of the continuous secondary fiber is disposed toward a first face of the knit hemostatic bandage and the loop of the continuous glass fiber is disposed toward a second face of the knit hemostatic bandage, the second face opposite the first face, and (ii) a second configuration in which the loop of the continuous secondary fiber is disposed toward the second face of the knit hemostatic bandage and the loop of the continuous glass fiber is disposed toward the first face of the knit hemostatic bandage, the knit hemostatic bandage having a gauge of 20 stitches per inch, and wherein due to a relative motion of the loops of the continuous secondary fiber and the loops of continuous glass fiber that occurs responsive to deformation of the knit hemostatic bandage, the knit hemostatic bandage is provided with an overall Young's modulus of elasticity of between 0.05 MPa and 1 MPa.

* * * * *